US005459879A

United States Patent [19]
Fuchs

[11] Patent Number: 5,459,879
[45] Date of Patent: Oct. 24, 1995

[54] PROTECTIVE COVERINGS

[75] Inventor: Ingbert E. Fuchs, DeSoto, Tex.

[73] Assignee: Board Of Regents, The University of Texas System, Austin, Tex.

[21] Appl. No.: 678,838

[22] Filed: Apr. 1, 1991

Related U.S. Application Data

[63] Continuation-in-part of Ser. No. 359,474, May 22, 1989, abandoned, and a continuation-in-part of Ser. No. 422,913, Oct. 17, 1989, abandoned.

[51] Int. Cl.$^6$ .............................. A41D 19/00; A61F 6/04
[52] U.S. Cl. .............................. 2/161.7; 2/168; 128/844
[58] Field of Search .................................... 2/159, 161 R, 2/167, 168, 161.7; 128/844; 604/349

[56] References Cited

U.S. PATENT DOCUMENTS

| | | | |
|---|---|---|---|
| 1,954,262 | 4/1934 | Potter . | |
| 2,120,406 | 6/1938 | Hansen | 264/306 X |
| 2,148,832 | 2/1939 | Raynolds | 260/111 |

(List continued on next page.)

FOREIGN PATENT DOCUMENTS

| | | |
|---|---|---|
| 1917699 | 4/1969 | Denmark . |
| 0089780A2 | 3/1983 | European Pat. Off. . |
| 0089181A1 | 3/1983 | European Pat. Off. . |

(List continued on next page.)

OTHER PUBLICATIONS

PCT International Search Report dated May 21, 1992 for International Patent Application No. PCT/US91/08623.
Rabinovich et al., "Direct Measurements of Long–Range Surface Forces in Gas and Liquid Media," *Advances in Colloid and Interface Science*, vol. 16, pp. 63–78 (1982).
Wright, et al., "Mechanisms of Glove Tears and Sharp Injuries Among Surgical Personnel," Jama, vol. 266, No. 12, pp. 1668–1671 (Sep. 25, 1991).
*Plastics Fabrication and Uses*, vol. 74, No. 13928m (1971).
*Chemical Abstracts*, vol. 78, No. 31154t (1973).
*Nuclear Technology*, vol. 80, No. 127274z (1974).
Rigel et al., "Modification of Surgical Gloves Prevent Exposure to Hepatitis During Hair Transplantation Surgery," *J. Dermatol. Surg. Oncol.*, 9:2, pp. 114–115 (Feb. 1983).
"Standard Specification for Rubber Surgical Gloves", D3577–78, pp. 477–485, American Society for Testing and Materials (Jul. 1978).
"Standard Specification for Rubber Finger Cots," D3772–86, pp. 523–525, *American Society for Testing and Materials* (May 1986).
*Webster's Third New International Dictionary*, at pp. 706–710 (1986).
Hickes, et al., "Inactivation of HTLV–III/LAV–Infected Cultures of Normal Human Lymphocytes by Monoxynol-9 In Vitro," *The Lancet*, pp. 1422–1423 (Dec. 21/28, 1985).
Spire, et al., "Inactivation of Lymphadenopathy Associated Virus by Chemical Disinfectants," *The Lancet*, pp. 899–901 (Oct. 20, 1984).
Grossgebauer, "Virus Disinfection," *Disinfection*, pp. 103–148 (1970).
Dialog Search Report.
Annex to the International Search Report of the International Patent Application.
PCT Written Opinion.

*Primary Examiner*—Paul T. Sewell
*Assistant Examiner*—Ted Kavanaugh
*Attorney, Agent, or Firm*—Arnold, White & Durkee

[57] ABSTRACT

A protective covering, such as a surgical glove, having two layers sandwiching a layer of protective solution, such that if the covering becomes punctured or torn, the substance releases to protect the user. The liquid layer has an average thickness of less than about 0.12 mm, such that it exerts a capillary force on the two glove layers, thereby providing a mechanical-like coupling effect. The protective solution may include a dye for a visual indication of punctures or tears in the outer layer. The layers may be adhered together at desired points to restrict the layers from peeling apart during use. Various methods for making such protective coverings are disclosed.

14 Claims, 4 Drawing Sheets

U.S. PATENT DOCUMENTS

| | | | |
|---|---|---|---|
| 2,281,436 | 4/1942 | Hershberger | 260/735 |
| 2,410,460 | 11/1946 | Robinson . | |
| 2,586,674 | 2/1952 | Lönne . | |
| 2,792,835 | 5/1957 | Ferguson . | |
| 2,983,705 | 5/1961 | Baldwin et al. | 260/45.8 |
| 2,983,707 | 5/1961 | Baldwin et al. | 260/45.9 |
| 3,110,035 | 11/1963 | LaHue . | |
| 3,121,877 | 2/1964 | Gintner . | |
| 3,342,182 | 9/1967 | Charos . | |
| 3,633,216 | 1/1972 | Schonholtz . | |
| 3,672,351 | 6/1972 | Ubersax et al. . | |
| 3,813,695 | 6/1974 | Podell, Jr. et al. | 2/168 |
| 3,854,228 | 12/1974 | Conroy | 36/71 |
| 3,874,000 | 4/1975 | Altman . | |
| 3,883,899 | 5/1975 | Ganz | 2/168 |
| 3,898,253 | 8/1975 | Buckler et al. | 260/42.47 |
| 3,911,501 | 10/1975 | Seltzer . | |
| 3,975,775 | 8/1976 | Alsop . | |
| 4,070,713 | 1/1978 | Stockum | 2/168 |
| 4,143,423 | 3/1979 | Sternlieb . | |
| 4,185,330 | 1/1980 | Stager . | |
| 4,214,321 | 7/1980 | Nuwayser . | |
| 4,218,779 | 8/1980 | Hart et al. | 2/168 |
| 4,332,243 | 6/1982 | Gutnick | 128/844 |
| 4,432,357 | 2/1984 | Pomeranz . | |
| 4,442,147 | 4/1984 | Schirmer | 428/35 |
| 4,446,860 | 5/1984 | Gutnick . | |
| 4,471,538 | 9/1984 | Pomeranz et al. . | |
| 4,482,577 | 11/1984 | Goldstein et al. . | |
| 4,486,562 | 12/1984 | Fischer | 524/156 |
| 4,499,154 | 2/1985 | James et al. | 428/494 |
| 4,548,844 | 10/1985 | Podell et al. . | |
| 4,575,476 | 3/1986 | Podell et al. | 428/494 |
| 4,588,646 | 5/1986 | Athey, Jr. | 428/457 |
| 4,597,108 | 7/1986 | Momose | 2/168 |
| 4,657,021 | 4/1987 | Perry et al. | 128/630 |
| 4,668,224 | 5/1987 | Lentz et al. . | |
| 4,696,065 | 9/1987 | Elenteny | 2/168 |
| 4,742,578 | 5/1988 | Seid . | |
| 4,771,482 | 9/1988 | Shlenker . | |
| 4,795,425 | 1/1989 | Pugh . | |
| 4,843,014 | 7/1989 | Cukier . | |
| 4,864,661 | 9/1989 | Gimbel | 2/167 |
| 4,881,277 | 11/1989 | Hogle | 2/161 R X |
| 4,892,779 | 1/1990 | Leatherman et al. | 428/220 |
| 4,919,966 | 4/1990 | Shlenker . | |
| 4,930,522 | 6/1990 | Busnel et al. | 128/844 |
| 4,977,903 | 12/1990 | Haines | 128/844 X |
| 5,024,852 | 6/1991 | Busnel et al. | 2/161 R X |
| 5,045,341 | 9/1991 | Shlenker | 2/168 X |

FOREIGN PATENT DOCUMENTS

| | | |
|---|---|---|
| 0178856 | 10/1985 | European Pat. Off. . |
| 0300814A2 | 7/1988 | European Pat. Off. . |
| 0299802 | 7/1988 | European Pat. Off. . |
| 0306389 | 8/1988 | European Pat. Off. . |
| 0328421A2 | 2/1989 | European Pat. Off. . |
| 306389 | 3/1989 | European Pat. Off. . |
| 2616062 | 12/1988 | France . |
| 61-14242 | 1/1986 | Japan . |
| 61-9448 | 1/1986 | Japan . |
| 61-152449 | 7/1986 | Japan . |
| 326719 | 6/1929 | United Kingdom . |
| 540241 | 4/1942 | United Kingdom . |
| 2208358 | 3/1989 | United Kingdom . |
| WO84/00908 | 3/1984 | WIPO . |
| WO86/05391 | 9/1986 | WIPO . |
| WO90/14048 | 9/1990 | WIPO . |

PROTECTIVE COVERINGS

This is a continuation-in-part of applications Ser. Nos. 359,474 filed on May 22, 1989, and 422,913 filed on Oct. 17, 1989 both abandoned.

BACKGROUND OF THE INVENTION

1. Field of the Invention

This invention relates to protective coverings (e.g., gloves and condoms) for human body members, and methods for making such protective coverings. More particularly, this invention relates to coverings such as protective gloves which may be used for various purposes, including, for example, surgery or other medical procedures, or protection from hazardous chemical substances.

2. Description of the Related Art

The design of protective gloves represents a struggle of competing interests. To increase the protective nature of the glove intuitively requires increasing the thickness of the glove material. However, by increasing the thickness of the glove material, the sense of touch for the wearer of the gloves is increasingly hampered. Thus, the glove designer must find a suitable compromise between safety and sense of touch.

This problem is particularly acute in the area of surgical gloves. The sense of touch in the hands of a surgeon is important for the proper handling of delicate instruments and the proper execution of precise surgical procedures. However, it is also desirable that the surgeon be protected from biohazardous agents which the surgeon may be exposed to from the patient. For example, the surgical patient may carry viruses such as HIV (Human Immunodeficiency Virus) or hepatitis. During surgery, the surgeon's gloves are frequently cut or punctured, exposing the surgeon to infection.

Also, it is desirable to protect the patient from germs on the surgeon's or technician's hands. Although medical personnel, of course, typically scrub their hands before performing surgical procedures, some germs may remain and be exposed to the patient upon puncturing or tearing the surgical gloves.

Surgical gloves known to the Applicant are generally made of latex, vinyl, or neoprene, i.e. thin elastic materials which provide reasonable tear resistance and allow for satisfactory sense of touch. However, the gloves can be easily torn or punctured with sharp surgical instruments. Furthermore, it is difficult for the surgeon to detect a small tear or puncture in the glove material during surgery since such a puncture is difficult to see, especially if the gloves are covered with a patient's body fluids. Thus, the surgeon has little warning of exposure.

In the chemical or hazardous material preparation and handling area, disadvantages in present gloves also exist. Although the sense of touch for these areas may not be as important as that for the surgeon, there is also often a risk or danger even with thicker protective gloves. The glove material may be degraded or penetrated after a period of time by various chemicals which the chemist handles.

Protective coverings for other parts of the body also exist. For example, finger cots (i.e. glove-like coverings which cover only one finger) are used in medical procedures particularly in rectal and vaginal examinations. Condoms are used to cover the male reproductive organ during intercourse. In addition to the obvious purpose of a condom to trap semen and thereby minimize the possibility of pregnancy resulting from intercourse, condoms are also used to protect the partners from infections by sexually transmitted diseases. This has become increasingly important over recent years in preventing the spread of HIV.

In these and other protective coverings, similar problems and concerns exist, i.e. danger of tearing or ripping the covering balanced against the desire for sensitivity.

Thus it is an object of this invention to provide protective coverings which address the disadvantages experienced by the above-described coverings.

SUMMARY OF THE INVENTION

In one broad aspect, the present invention provides a protective covering for a human body member, the protective covering having an inner and outer layer. A layer of protective solution (such as an antimicrobial solution) is disposed between the inner and outer layers, and an impermeable seal is provided between the layers to contain the protective solution therebetween. The solution layer is less than about 0.12 millimeter (mm) average thickness, such that capillary forces are exerted on the two covering layers, thereby providing a mechanical-like coupling between the two covering layers.

The term "protective covering" is used to mean any covering used to protectively cover a human body member. The term "human body member" is used broadly to include all limbs and external protrusions of the human body, e.g., fingers, hands, arms, toes, feet, legs, head, penis, etc. In many situations, a human body member may be exposed to biohazardous substances such as infected body fluids, or hazardous chemicals. Coverings are often used to protect body members from exposure to hazardous substances. Thus, the term "protective covering" includes such items as gloves, finger cots, condoms, and the like.

In a preferred embodiment, the present invention provides a surgical glove having an inner and outer layer. A layer of antimicrobial solution is disposed between the inner and outer layers, and an impermeable seal between the layers is provided. As stated above, the solution layer is less than 0.12 mm in average thickness to provide a mechanical-like capillary coupling between the glove layers.

To maximize the capillary force exerted by the liquid layer, the average thickness of such layer is preferably between about 0.01 and 0.09 mm, most preferably between about 0.025 and 0.05 mm. Further, the liquid layer is preferably of substantially uniform thickness.

The term "antimicrobial solution" means herein a solution, typically aqueous, capable of killing or inactivating infectious agents, such as bacteria or virus. Thus, the term includes, for example, virucides, bactericides, antiseptic solutions, antiviral solutions, antibacterial solutions, etc. The term also includes spermicidal solutions, particularly applicable when the protective garment provided by the invention is a condom. The spermicidal solution used is preferably additionally virucidal and/or bactericidal.

The term "impermeable seal" is used to mean a seal which is substantially both fluid-tight and air-tight. The seal should be fluid-tight to prevent leakage of the protective solution between the layers, and should be air-tight to facilitate mechanical coupling between the two layers resulting from capillary forces exerted by the protective solution.

Typical virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

The glove of this invention can provide improved protection over single layer surgical gloves. If the layers of the glove are punctured or torn during surgery, the antimicrobial solution releases and attacks infectious agents before reaching the surgeon's hands, thus protecting the surgeon during operating procedures. Furthermore, when the glove becomes punctured during use, it may act to protect the patient from exposure to germs which may exist on the surgeon's hands. Tearing or puncturing the glove may provide quick and thorough release of the antimicrobial solution disposed between the layers.

Applicant has found that sense of touch is not significantly diminished by the double layers. By providing a solution layer of thickness in the ranges described above, capillary forces exerted by the liquid solution provide a mechanical-like coupling between the glove layers, so that the sense of touch for the wearer of the gloves is not significantly diminished.

In a preferred embodiment, the antimicrobial solution comprises a virucidal solution, such as aqueous nonoxynol-9. This substance is an effective virucide against such viruses as HIV and hepatitis, and thus provides a glove being particularly useful for performing medical procedures on infected patients. Preferably, the aqueous nonoxynol-9 has a concentration of between about 0.05% and 5% (volume/volume). Most preferably, the concentration is between about 0.25% and 1% (volume/volume). It is known that a concentration in this range is effective for killing viruses. Higher concentrations can also be used but may be irritable if contacted with the eyes.

In another embodiment, the antimicrobial solution comprises a bactericidal solution. Of course, the antimicrobial solution could include both virucidal and bactericidal agents.

In a preferred embodiment of a surgical glove provided by the present invention, the antimicrobial solution includes a dye. This embodiment provides an effective means for showing the surgeon the precise location of a tear or puncture in the glove. Thus, if the outer layer of the glove is punctured, the dye will seep out of the puncture hole and stain the area around the hole. If the inner layer is also punctured, the dye will seep through the inner hole and stain the surgeon's hand at the location of the puncture. This provides the surgeon the precise location of exposure so that the surgeon can decontaminate the area of puncture.

Many suitable dyes are available for use with this invention. A dye should preferably be selected which is FDA approved for internal and external use so as not to harm the patient or surgeon. Preferably, the dye is selected so that its color is easily detectable in a blood environment. Suitable dyes incudes FDA approved FD&C colors, for example, FD&C Blue #2 (MERCK Index #4835) and FD&C Green #2 (MERCK Index #5312). These two dyes are particularly preferred since they have FDA approval for use in food, drugs, and cosmetics, have not been found to be carcinogenic, and provide good indications of puncture in use with the present invention due to their intense colors. Preferably, the concentration of the dye in the antimicrobial solution is between about 0.3 to 0.5 grams/liter, providing a good compromise between economics and tear indication.

Many dyes are also bactericidal and thus provide the further function of attacking infectious agents. Another advantage provided by use of such dyes is that they can not generally be washed off with water. Thus, if the glove is punctured and the user's hand is stained by the dye, he must use alcohol to remove the stain, alcohol also being a bactericide. Thus, the area of the puncture is decontaminated while the dye stain is washed off.

Preferably, the volume of the antimicrobial solution disposed between the layers of an average-sized glove (e.g. size 7.5–8.5) is between about 2 and 3 milliliters. For a size 8.5 glove (surface area approximately 650 $cm^2$), this volume of liquid provides a solution layer thickness of around 0.03 to 0.05 mm, thereby providing good capillary coupling between the glove layers.

In a preferred embodiment, the inner and outer layers are made of latex. Alternatively, the layers may comprise vinyl or neoprene. Latex provides adequate tear resistance for surgical procedures and allows for a good sense of touch for the wearer.

In a preferred embodiment, the inner layer may include a rough outer surface. Alternatively, the outer layer may include a rough inner surface. This may provide the advantage of preventing the antimicrobial solution from being completely squeezed away from any glove areas which are compressed during normal usage.

For applications when one may be exposed to harmful chemicals, such as during handling or preparation of chemicals or other hazardous substances, another embodiment of the present invention provides a protective glove. The protective glove includes an inner layer, an outer layer, an impermeable seal between the inner and outer layers, and a layer of neutralizing solution (thickness as described above) disposed between the inner and outer layers.

The neutralizing solution disposed between the inner and outer layers can be appropriately selected for the particular application for which the glove is to be used. Preferably, the neutralizing solution should be selected such that if the outer layer of the glove is punctured or permeated, the neutralizing solution will neutralize the chemicals to which the glove is exposed and thus protect the hands of the wearer of the glove.

For example, if a Chemist is to be handling acids, the neutralizing solution selected should be a basic or buffering solution which could neutralize the acid upon puncture of the glove before reaching the chemist's hands. As another example, if a person were handling neurotoxins one might place appropriate enzymatic agents between the glove layers which could cleave the neurotoxins upon contact.

Since the sense of touch for a chemist is usually not as critical as that for a surgeon, a thicker and more protective material than latex is preferably selected for the protective glove. For example, the inner and outer layers may be made of neoprene, nitrile, or any other suitable materials which are resistant to the types of materials to be handled and which are resistant to tearing or puncture.

Since the appropriate neutralizing solution disposed between the layers may vary depending upon the chemicals or materials to be handles, the seal between the layers preferably includes a zip lock seal. In this manner, the user of the glove can temporarily open the seal, place the appropriate neutralizing solution between the glove layers, and reseal the glove.

Additionally, the material between the glove layers may included a pH or other indicator which would change colors after a passage of time to indicate that the neutralizing agent has been used up, such that the gloves may no longer be effective. Upon such indication, the user could replace the old gloves with a new pair.

In a preferred embodiment, the protective solution includes a dye to give a visible warning upon release if the glove is leaking or becomes punctured. That is, the dye upon release will stain the area of puncture.

Another embodiment of the present invention provides a surgical glove including a dye associated with the glove in such a manner as to produce a visible stain if the glove becomes punctured or torn at the location of such puncture or tear.

The invention also extends to a finger cot having an inner layer, an outer layer, an impermeable seal between the layers, and a layer of antimicrobial solution (thickness as described above) disposed between the layers. The finger cot is substantially similar to the surgical glove described above, except that the finger cot is configured and used to cover only a single finger as opposed to an entire hand. The preferred embodiments of materials discussed above in relation to surgical gloves also apply to finger cots. Thus, for example, the antimicrobial solution of the finger cot preferably includes a dye.

The invention further provides a condom having an inner and outer layer, an impermeable seal between the layers, and a layer of antimicrobial solution (thickness as described above) disposed between the inner and outer layers. Preferably, the antimicrobial solution comprises a spermicidal solution, such as nonoxynol-9. Nonoxynol-9 is particularly preferred since it also acts as a virucidal agent for protection against HIV and hepatitis.

One potential problem which can arise with the double (or multi) layer protective coverings provided by this invention is that the two layers may tend to peel away from each other during use. This potential problem is most likely to arise when the covering is inserted into and removed from a tight passage, as will typically occur when using a glove, finger cot or condom. To reduce this problem, the layers of the covering may be sealed (e.g., by heat stamping or gluing) at a plurality of points, thereby physically adhering the two layers at those points. This will reduce the likelihood of disassembly of the covering during use.

It should be appreciated that the protective ability of the covering may be reduced at the sealed points, since a puncture of the covering at that precise location might not cause the release of the protective solution disposed between the layers. This is not likely to present a significant concern in relation to condoms and finger cots, since sharp objects are not generally encountered when using those items. Nevertheless, the potentially reduced protection of the covering should be appreciated and considered when selecting the number and pattern of sealed points on the covering.

Another broad aspect of this invention provides methods for making protective gloves, e.g., surgical gloves. One such method comprises the steps of providing a first glove on a hand-shaped form, the first glove having a hand portion and a wrist portion; dipping the first glove into an antimicrobial solution; placing a second glove having a hand portion and a wrist portion on the hand-shaped form over the first glove, and sealing the wrist portions of said gloves together, such that the antimicrobial solution is contained as a layer between the first and second gloves, the solution layer having an average thickness of less than about 0.12 mm.

A second method provided by this invention comprises the steps of providing a first glove on a hand-shaped form, the first glove having a hand portion and a wrist portion; placing a second glove on the hand-shaped form over the first glove, the second glove having a hand portion and a wrist portion; placing an antimicrobial solution between the first and second gloves, and sealing the wrist portions of said gloves together, such that the antimicrobial solution is contained as a layer (thickness as described above) between the first and second gloves.

The term "hand-shaped form" is used herein broadly to mean any structure having the shape of a human hand, e.g., a conventional porcelain former. The term also encompasses an actual human hand.

The initial step in each of the two above-described methods comprises providing a first glove on a hand-shaped form. This can be accomplished, for example, by obtaining a glove from a commercial or other available source and stretching the glove over a hand-shaped form. Alternatively, it can be accomplished by dipping a hand-shaped form into latex or other material to coat the form with a layer of the material, and drying the layer to form the first glove on the form.

A third method for making a protective glove provided by this invention comprises the steps of providing a first glove having a hand portion and a wrist portion; exposing the exterior surface of the first glove to a vacuum to expand said glove; placing an antimicrobial solution on the interior surface of the first glove; inserting a second glove having a hand portion and a wrist portion into the expanded first glove; removing the vacuum from the exterior surface of the first glove; and sealing the wrist portions of the first and second gloves together to contain the antimicrobial solution as a layer (thickness as described above) between the first and second gloves.

The first and second gloves in all three methods described above may be, for example, conventional latex surgical gloves, or gloves made of some other material.

Finally, this invention provides a fourth method for making a protective glove comprising the steps of providing an enclosed bag or balloon (i.e., an enveloped sheet of material) having two opposing hand-shaped sections; puncturing one of the hand-shaped sections; applying a vacuum to the interior of the punctured hand-shaped section such that the opposing hand-shaped section is drawn into said punctured section; releasing the vacuum; injecting an antimicrobial solution between the two hand-shaped sections and sealing the puncture, such that the antimicrobial solution is contained as a layer (thickness as described above) between said sections. The enclosed bag of material may be produced in a negative form based on two negative hand-shaped spaces.

A preferred embodiment of each of the above-described methods comprises an additional step of adhering the two hand portions or sections together at a plurality of points. This provides the advantage of restricting disassembly or peeling apart of the two hand portions or sections during use of the glove.

The hand portions or sections may be adhered together in a variety of ways, e.g., by glue or double-sided adhesive tape.

In a preferred embodiment, the adhering step is accomplished by spot-vulcanizing the hand portions together at a plurality of points. In this embodiment, the first and second gloves (or the enclosed bag in the fourth method described above) may comprise unvulcanized (i.e., green strength) latex. After spot-vulcanizing the hand portions or sections together at the desired points, the entire glove assembly may then be vulcanized. Due to the high temperature involved in such vulcanization, the antimicrobial solution disposed within the glove assembly preferably comprises a degassed liquid, so that the liquid will not emit gas during the vulcanization step.

BRIEF DESCRIPTION OF THE DRAWINGS

This invention is now described by reference to the appended drawings which illustrate particular preferred embodiments of this invention.

DETAILED DESCRIPTION OF PREFERRED EMBODIMENTS

Figures 1, 1A:
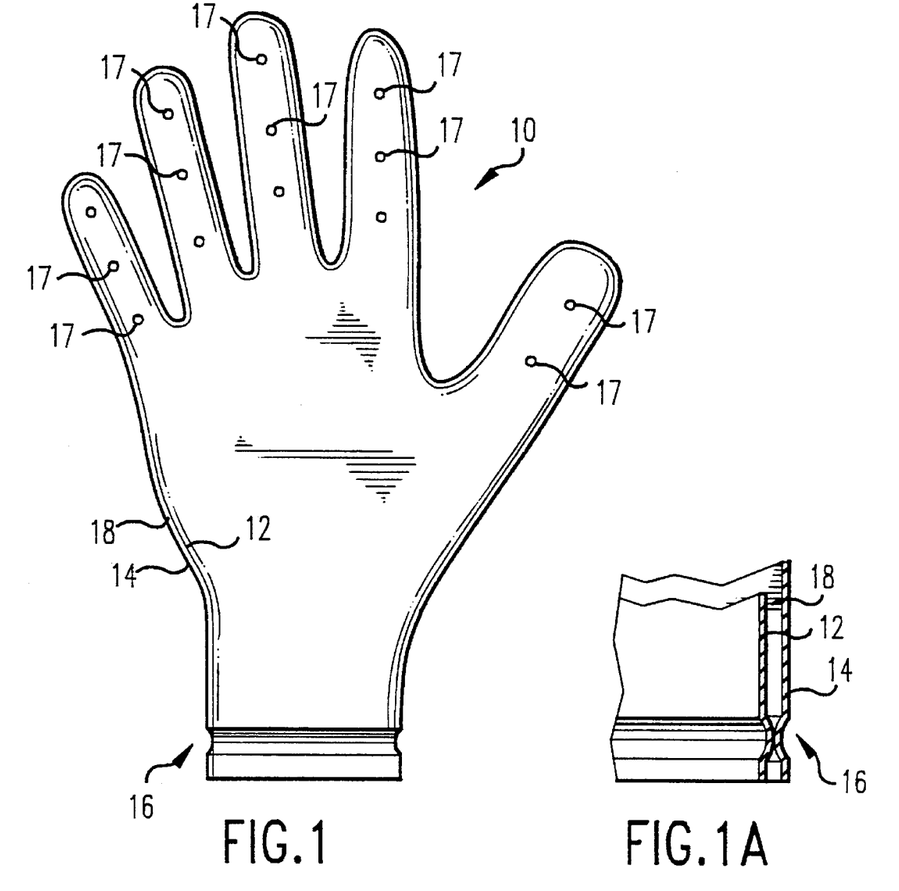
FIG. 1 is a side view of a glove prepared according to the present invention.
FIG. 1A is an enlarged, fragmentary, sectional side view illustrating the impermeable seal between the inner and outer layers of the glove of FIG. 1.

Referring now to FIG. 1, a preferred embodiment of the present invention is shown. A double layer glove 10 is illustrated having an inner layer 12, an outer layer 14, an impermeable seal 16 between the inner layer 12 and the outer layer 14, and a protective solution 18 disposed between the inner layer 12 and the outer layer 14. The solution layer 18 has an average thickness of less than about 0.12 mm, preferably between about 0.01 and 0.09 mm, even more preferably between about 0.025 and 0.05 mm, thereby maximizing the capillary coupling force between glove layers 12 and 14.

This glove is suitable for a broad range of applications, depending upon the selection of material for the inner and outer layers 12 and 14 and the protective solution 18. For use as a surgical glove, the inner and outer layers 12 and 14 are preferably made of latex. For such a surgical glove 10, protective solution 18 preferably comprises an antimicrobial solution. The antimicrobial solution preferably comprises a virucidal agent such as nonoxynol-9. The antimicrobial solution may also or alternatively include a bactericidal solution.

In a preferred embodiment, the antimicrobial solution 18 includes a dye. The dye will stain the area surrounding a puncture or tear in the glove, giving the surgeon a visual means for detecting areas of exposure.

In a preferred embodiment of the invention, the antimicrobial solution comprises nonoxynol-9 having a concentration of between about 0.05%–5% (v/v), most preferably about 0.5% (v/v), and a dye comprising FD&C Blue #2 having a concentration of between about 0.3 and 0.5 g/l.

In one preferred embodiment, the inner layer 12 includes a rough outer surface (i.e., the surface exposed to the antimicrobial solution 18). Single layer latex gloves are commercially available, wherein one may specify the roughness or coarseness of the surfaces of the glove.

In a preferred embodiment, the layers 12 and 14 are sealed (i.e., adhered) together at a plurality of points to reduce the likelihood that the layers will be peeled apart during use. As shown in FIG. 1, the fingers of the glove 10 may include a plurality of points 17 where the layers 12 and 14 have been adhered together. This feature is particularly advantageous when the fingers are used to explore or examine tight places. As illustrated in FIG. 1, the adhered points 17 are preferably located at the dorsal midpoint of the distal, middle, and proximal phalanges of each finger. By locating the points at the dorsal portion of the glove 10, sensitivity is not substantially impaired, but disassembly of the layers is restricted.

The adhered points may be formed by heating and pressing the inner and outer layers together at the desired places for a sufficient length of time for a seal to form. Alternatively, the layers may simply be glued together, or stuck together with double-sided adhesive tape, available commercially from, e.g., the 3M Company.

Figure 2:
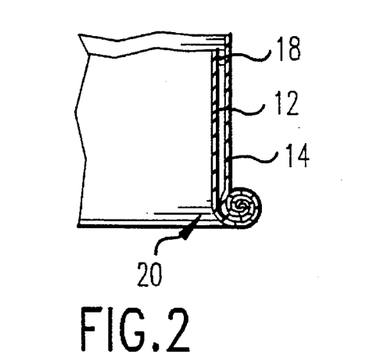
FIG. 2 is a fragmentary, sectional side view illustrating an alternate impermeable seal between the inner and outer layers of a glove in accordance with the present invention.
Figure 3:
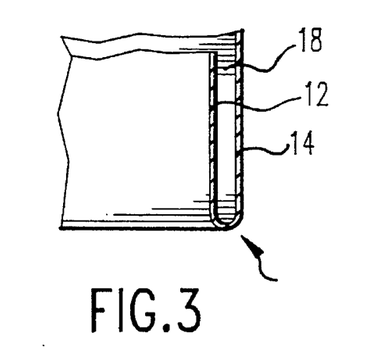
FIG. 3 is also a fragmentary, sectional side view showing another alternative of an impermeable seal.

The impermeable seal between the inner and outer layers 12 and 14 may take a variety of forms as illustrated in FIGS. 1A, 2 and 3. In FIG. 1A, the inner and outer layers 12 and 14 proximate the wrist area of the glove have been vulcanized or heat stamped to provide an impermeable seal 16. The seal 16 can be formed by simply applying heat and pressing the inner and outer layers 12 and 14 together around the circumference of the wrist area for a sufficient length of time for a seal to form.

Alternatively, inner layer 12 and outer layer 14 may be glued together to form an impermeable seal 20 as shown in FIG. 2. For example, with respect to a latex surgical glove, a latex glue can be conveniently used. Such glues are commercially available, e.g., 2141 Rubber Adhesive from the 3M Company. Alternatively, commercially available rubber cements can be used to create the seal between the layers. As a further alternative, shown in FIG. 3, inner layer 12 and outer layer 14 may be formed of a continuous sheet of material such that an impermeable seal 22 is provided by the roll connecting the inner and outer layers 12 and 14. Other fluid-tight seals may be used, for example, tape adhesive on both sides or a zip lock seal.

For chemical handling or preparation applications, the inner and outer layers 12 and 14 shown in FIG. 1 preferably comprise either neoprene or nitrile. A neutralizing solution 18 is disposed between the inner and outer layers 12 and 14. Furthermore, the seal 16 is preferably a zip lock type seal, so that the user can select and place an appropriate neutralizing solution between the layers depending upon the particular chemicals to be handled.

Several methods of preparing gloves provided by the present invention will now be described. These preparations will be discussed in the context of surgical gloves, although it should be understood that analogous preparations may be performed for other types of gloves and protective coverings.

In one preferred method, one places a first glove on his hand (or hand-shaped form). This first glove will eventually form the inner layer of a double-layer glove. The preparer of the glove dips his gloved hand into an antimicrobial solution and removes his hand from the solution. The preparer then places a second glove on his hand over the first glove. The second glove thus forms the outer layer of the double-layer glove. To form an impermeable seal between the first and second gloves, the preparer may peel a portion of the second glove away from his wrist. The preparer then applies glue or double adhesive tape to the outer surface of the first glove around the periphery proximate the wrist of the glove. The preparer then peels the wrist area of the second glove back over the first glove to form a glue seal.

In another preferred method, one places a first glove on a hand-shaped form. Next, glue or double-sided adhesive tape is placed at various points on the exterior of the first glove. Next, a second glove is placed over the first glove, whereby the glue or double-sided adhesive tape adheres the two gloves together at a plurality of points. Next, an antimicrobial solution is placed between the first and second gloves, e.g., by injecting the solution therebetween. Finally, the wrist portions of the two gloves are sealed (e.g., with glue or double-sided adhesive tape) to contain the antimicrobial solution between the two gloves.

In another preferred method, one dips a hand-shaped form (e.g., a porcelain former) in latex to form a layer of latex on the form. When the layer is sufficiently dry, a first glove is thereby provided on the hand-shaped form. A second green strength (i.e., unvulcanized) latex glove is placed over the first glove, and a degassed antimicrobial liquid is disposed between the two gloves. (This may be accomplished either by dipping the first glove in the degassed antimicrobial liquid prior to applying the second glove, or injecting the degassed antimicrobial liquid between the two gloves after applying the second glove). Next, the wrist portions of the two gloves are adhered together by vulcanization to form an impermeable seal, thereby containing the antimicrobial solution between the two gloves. The two gloves may be adhered together at a plurality of points by spot-vulcanizing them together at desired spots. Finally, the entire glove assembly is vulcanized.

Another suitable method of preparing a double-layer glove includes providing a first glove and exposing the exterior of the first glove to a vacuum environment. This first glove will eventually form the outer layer of the double-layer glove provided by the present invention. For example, the first glove may be inserted into a box through a box opening, wherein the wrist area of the first glove is temporarily sealed over the opening of the box in an air-tight arrangement. A vacuum is then applied to the interior of the box. This operates to expand the first glove like a balloon.

Next, a selected amount of antimicrobial solution is placed into the interior of the first glove. A second glove, which will form the inner layer of the double-layer glove, is now inserted into the expanded first glove. Preferably, the second glove is provided on a production form in the shape of a hand so that the second glove may be conveniently inserted in proper finger alignment with the first glove. The vacuum is then released and the first glove is released from the box opening. The first and second layers are then sealed proximate the wrist area.

A double-layer glove may be formed from a single piece of material, and thus provide a glove having a rolled seal as illustrated in FIG. 3. To make such a glove, a sheet of latex is first formed having two opposing glove-shaped sections. Such a sheet may be made using a negative form. Thus, one half of the sheet is in the shape of a hand, and the other half of the sheet is in the shape of an opposing hand. A puncture is made in one of the opposing hand sections and a vacuum is applied to the interior portion of that hand section. Due to the vacuum, the opposing hand section will be drawn into the first hand to provide a double layer glove. The hand section in which the puncture was made and vacuum applied forms the outer layer, and the opposing hand section forms the inner layer. The vacuum is then released and a selected amount of antimicrobial solution is injected between the two hand sections through the puncture opening in the outer glove section. The puncture opening is then sealed.

Figure 4:
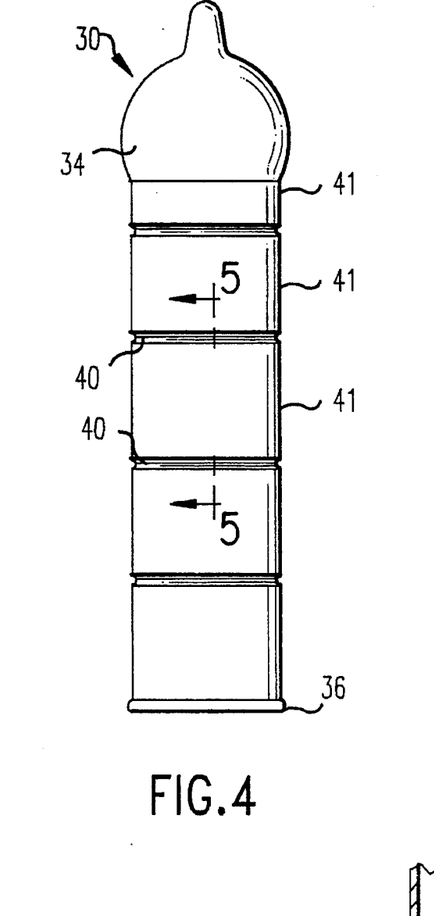
FIG. 4 is a side view of a condom prepared according to the present invention.
Figure 5:
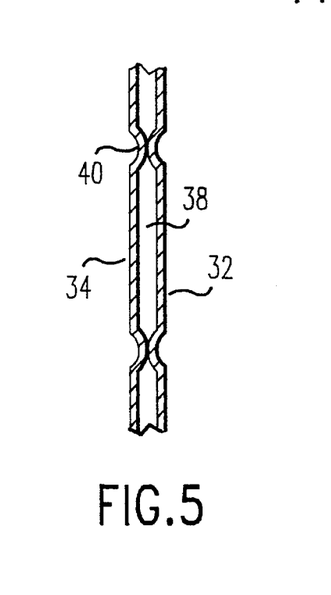
FIG. 5 is a fragmentary, sectional view of the condom taken at the position shown in FIG. 4.

Referring now to FIGS. 4 and 5, a preferred embodiment of a condom 30 as provided by the present invention is illustrated. The condom 30 includes an inner layer 32, and outer layer 34, and an impermeable seal 36 between the inner and outer layers at the rim of the condom. A layer of spermicidal solution 38 (thickness as described above), such as nonoxynol-9, is disposed between the inner layer 32 and outer layer 34. Nonoxynol-9 is preferred, as it is both spermicidal to reduce the risk of pregnancy and virucidal for protection against harmful viruses such as HIV. The layers may be made of materials conventionally used for making condoms.

In order to reduce the likelihood of the layers 32 and 34 from peeling apart during use, the layers may be sealed together at a plurality of points. In the embodiment shown, the condom 30 is provided with a plurality of circular heat stamped lines 40, dividing the condom into distinct compartments 41 along its length. In this arrangement, the protective fluid 38 may be prevented from squeezing to the base of the condom during use, as each heat stamped line 40 will restrict fluid flow between adjacent compartments 41. The heat stamped lines may be formed by heating and pressing the inner and outer layers together at the desired places for a sufficient length of time for a seal to form.

Figure 6:
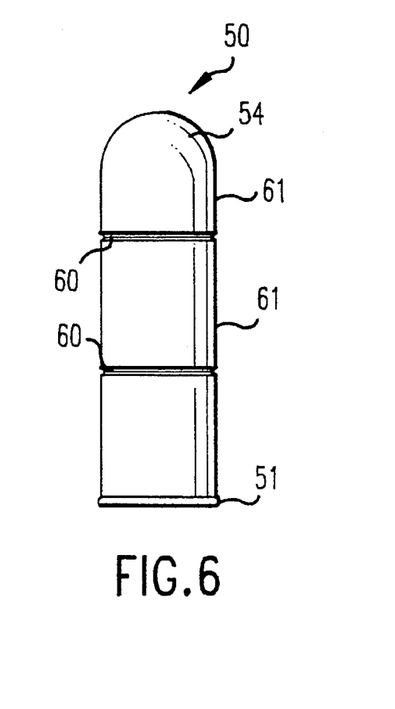
FIG. 6 is a side view of a finger cot prepared according to the present invention.

Referring now to FIG. 6, a preferred embodiment of a finger cot 50 is illustrated. Similar to the surgical glove described above, the finger cot 50 includes an inner layer, an outer layer 54, an impermeable seal 56 between the inner and outer layers, and a layer of antimicrobial solution (thickness as described above) disposed between the layers. (It should be noted that a sectional view of the sidewall of the finger cot would look substantially similar to FIG. 5). The preferred materials for use as the layers and antimicrobial solution discussed above in connection with surgical gloves also apply to the finger cot 50.

Since finger cots are conventionally used for procedures such as rectal or vaginal examinations, it is desirable to seal the inner layer 52 and outer layer 54 together at a plurality of points to reduce the likelihood of disassembly during use. In the embodiment shown, the finger cot 50 is heat stamped with several circular lines 60, compartmentalizing the finger cot into isolated sections 61. As with the condom described above, this embodiment prevents the antimicrobial solution from accumulating at the base of the finger cot during use.

EXAMPLE

The following experiment was designed to demonstrate the capillary coupling force exerted by a liquid layer between two latex surfaces as a function of the thickness of the liquid layer. This was accomplished by measuring the average failure load ("AFL") in $g/cm^2$, between two latex-coated glass carriers having a fluid layer of varying thickness therebetween.

Procedure

Figure 7:
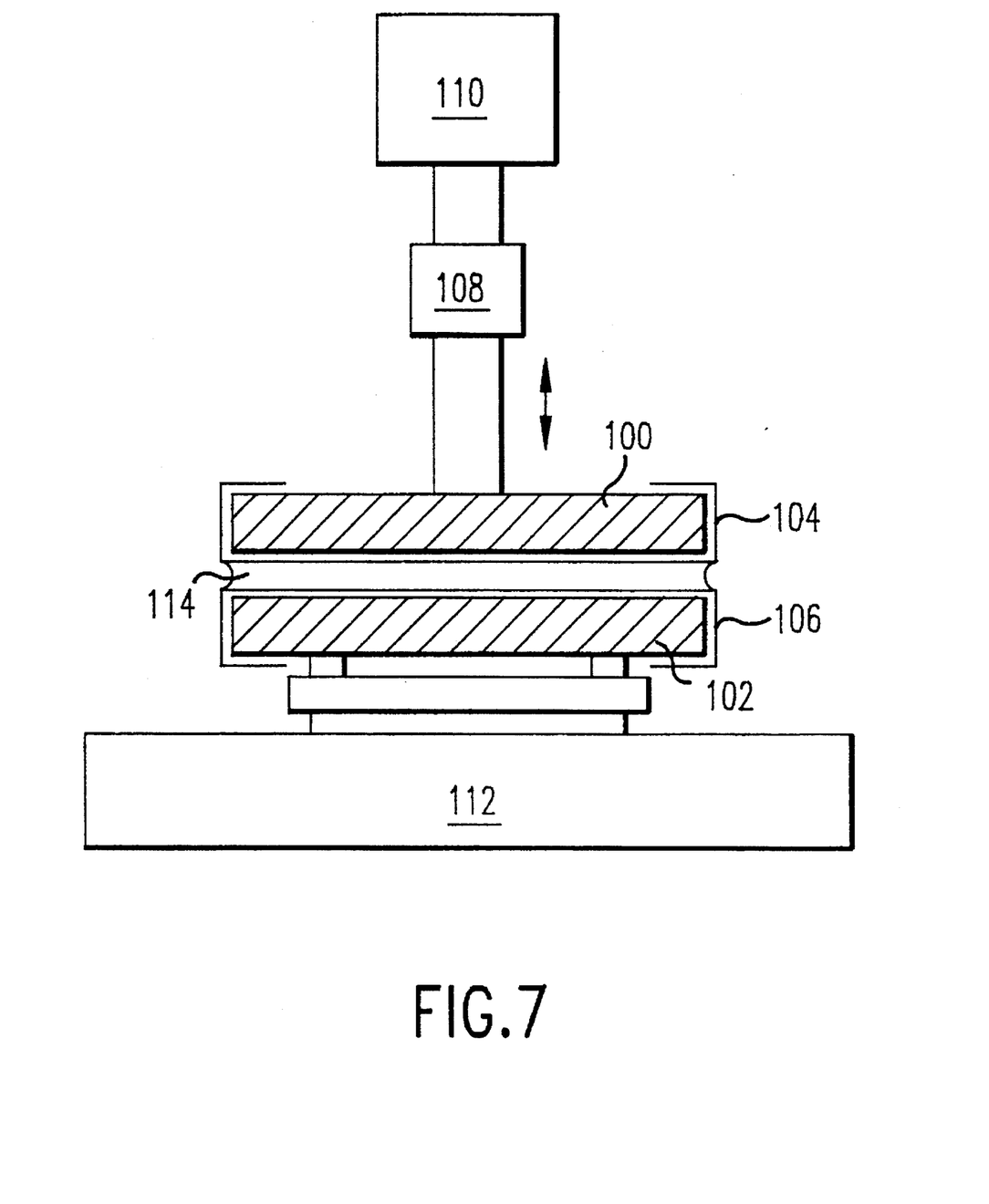
FIG. 7 is a schematic diagram of the apparatus used in the example below.

FIG. 7 illustrates the apparatus used in the experiment. Two pieces of latex material 104 and 106 were glued onto the surface of two glass carriers 100 and 102, respectively. The pieces of latex were obtained from Travenol Triflex Sterile Latex Surgeons Gloves, size 8.5, in which powder had been removed by washing three times in 2 liters aqua bidest. The latex layers 104 and 106 were each 0.18 mm thick, while each glass carrier 100 and 102 was 6 mm thick.

Glass carrier 100 was mechanically connected to a micrometer 108 with 0.01 mm resolution. The micrometer 108 was driven by a stepping motor 110 at a rate of 1 mm/min.

Glass carrier 102 was preweighted with 300 g and connected to a rapidly indicating electronic balance 112. The contact area between the two carriers 100 and 102 was 2 in$^2$ (~25.81 cm$^2$).

Volumes ranging from 10 µl to 500 µl of colored bactericidal fluid 114, were pipetted onto the surface of carrier 102, and carrier 100 was lowered until the liquid 114 covered the entire contact area.

Carrier 100 was then lifted at a constant time rate by the stepper motor 110 via the micrometer 108. The maximum decrease in weight, indicated by the electronic balance 112, was reached shortly before rupture of the liquid layer 114 and noted.

Each experiment for a specific liquid volume was repeated seven times.

Results

Figure 8:
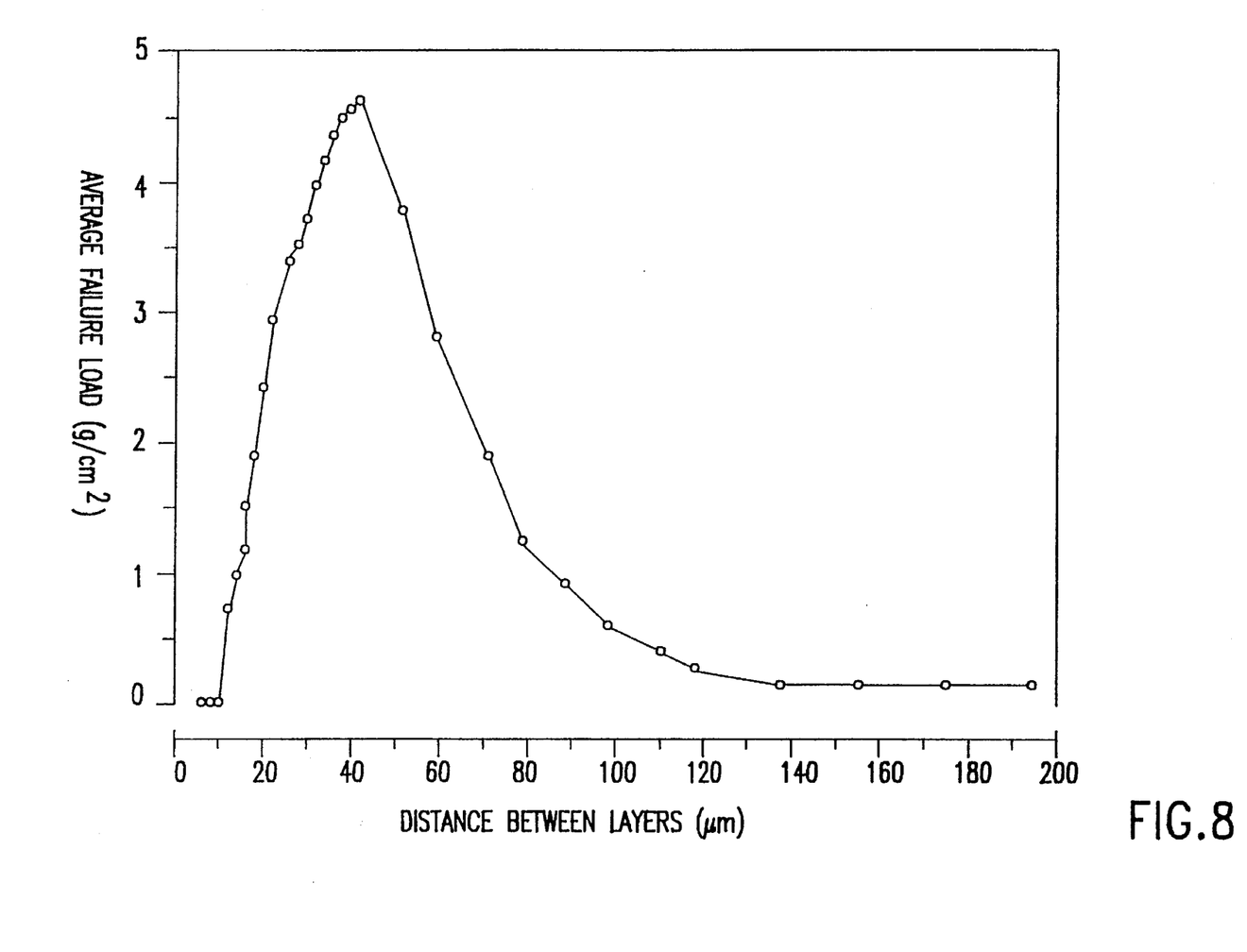
FIG. 8 is a plot of the experimental results of the example below.

The results of the experiment are shown in Table 1 and FIG. 8. The maximum AFL was reached at a liquid volume of around 100 µl (~0.039 mm fluid layer thickness). The AFL approached zero at volumes above 300 µl (~0.116 mm thick).

For comparison, the last column of Table 1 gives the required liquid volume, corresponding to the given liquid layer thickness, for a glove size 8.5 (surface area ~650 cm$^2$). Thus, for example, to obtain a fluid layer thickness of 0.039 mm between two size 8.5 gloves would require a fluid volume of about 2.518 ml.

The instant invention has been disclosed in connection with specific embodiments. However, it will be apparent to those skilled in the art that variations from the illustrated embodiments may be undertaken without departing the spirit and scope of the invention. For example, in connection with jobs where it is required that gloves be discarded after a certain amount of use, e.g. four hours, an absorption indicating substance might be placed between the glove layers to, e.g., change colors upon a certain degree of absorption.

What is claimed is:

1. A surgical glove comprising:

a first glove forming an inner layer;

a second glove forming an outer layer;

an impermeable seal between the inner and outer layers; and a single substantially continuous layer of antimicrobial solution disposed between the inner and outer layers, said solution layer having an average thickness of less than about 0.12 millimeter.

2. The surgical glove of claim 1, wherein the layer of antimicrobial solution has an average thickness of between about 0.01 and 0.09 millimeter.

3. The surgical glove of claim 1, wherein the layer of antimicrobial solution has an average thickness of between about 0.025 and 0.05 millimeter.

4. The surgical glove of claim 1, wherein the antimicrobial solution includes a dye.

5. The surgical glove of claim 1, wherein the inner layer includes a rough outer surface.

6. The surgical glove of claim 1, wherein the outer layer includes a rough inner surface.

TABLE 1

| LIQUID VOLUME (µl) | DISTANCE BETWEEN CARRIERS (LIQUID LAYER THICKNESS) (mm) | AVERAGE FAILURE LOAD (g/cm$^2$) | EQUIVALENT LIQUID VOLUME FOR GLOVE (ml/650 cm$^2$) |
|---|---|---|---|
| 10 | 0.004 | 0.000 | 0.252 |
| 15 | 0.006 | 0.000 | 0.378 |
| 20 | 0.008 | 0.000 | 0.504 |
| 25 | 0.010 | 0.697 | 0.630 |
| 30 | 0.012 | 0.969 | 0.756 |
| 35 | 0.014 | 1.124 | 0.881 |
| 40 | 0.015 | 1.434 | 1.007 |
| 45 | 0.017 | 1.860 | 1.133 |
| 50 | 0.019 | 2.402 | 1.259 |
| 55 | 0.021 | 2.867 | 1.385 |
| 60 | 0.023 | 3.371 | 1.511 |
| 65 | 0.025 | 3.487 | 1.637 |
| 70 | 0.027 | 3.681 | 1.763 |
| 75 | 0.029 | 3.952 | 1.889 |
| 80 | 0.031 | 4.184 | 2.015 |
| 85 | 0.033 | 4.339 | 2.141 |
| 90 | 0.035 | 4.456 | 2.267 |
| 95 | 0.037 | 4.494 | 2.392 |
| 100 | 0.039 | 4.611 | 2.518 |
| 125 | 0.048 | 3.719 | 3.148 |
| 150 | 0.058 | 2.751 | 3.778 |
| 175 | 0.068 | 1.860 | 4.407 |
| 200 | 0.077 | 1.162 | 5.037 |
| 225 | 0.087 | 0.814 | 5.666 |
| 250 | 0.097 | 0.504 | 6.296 |
| 275 | 0.107 | 0.310 | 6.926 |
| 300 | 0.116 | 0.116 | 7.555 |
| 350 | 0.136 | 0.000 | 8.814 |
| 400 | 0.155 | 0.000 | 10.074 |
| 450 | 0.174 | 0.000 | 11.333 |
| 500 | 0.194 | 0.000 | 12.592 |

7. The surgical glove of claim 1, wherein the first and second gloves each have a thickness of between about 0.2 and 0.5 millimeters.

8. The surgical glove of claim 1, wherein the inner and outer layers are adhered together at a plurality of points to restrict disassembly of said layers during use.

9. The surgical glove of claim 8, wherein the points at which the inner and outer layers are adhered together are located dorsally on the glove.

10. The surgical glove of claim 1 wherein capillary forces exerted by the antimicrobial solution provide a mechanical-like coupling between the glove layers.

11. A protective glove comprising:

a first glove forming an inner layer;

a second glove forming an outer layer;

an impermeable seal between the inner and outer layers; and a single substantially continuous layer of neutralizing solution disposed between the inner and outer layers, said solution layer having an average thickness of less than about 0.12 millimeter.

12. The protective glove of claim 11, wherein the impermeable seal comprises a fluid-tight, releasable seal.

13. The protective glove of claim 11, wherein the layer of neutralizing solution has an average thickness of between about 0.01 and 0.09 millimeter.

14. The protective glove of claim 11, wherein the layer of neutralizing solution has an average thickness of between about 0.025 and 0.05 millimeter.

* * * * *